US011508261B2

(12) United States Patent
Deffieux et al.

(10) Patent No.: US 11,508,261 B2
(45) Date of Patent: Nov. 22, 2022

(54) METHOD FOR OBTAINING A NUMERICAL MODEL ASSOCIATING AN OBJECTIVE MEASUREMENT TO A SUBJECTIVE SENSATION USING ULTRASOUND IMAGING TECHNIQUE AND ASSOCIATED DEVICE

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); SORBONNE UNIVERSITÉ, Paris (FR); UNIVERSITÉ PARIS DIDEROT - PARIS 7, Paris (FR); ECOLE SUPERIEURE DE PHYSIQUE ET DE CHIMIE INDUSTRIELLES DE LA VILLE DE PARIS, Paris (FR)

(72) Inventors: Thomas Deffieux, Paris (FR); Mickaël Tanter, Paris (FR); Jean-Luc Gennisson, Paris (FR); Zsolt Lenkei, Paris (FR); Mathieu Pernot, Paris (FR)

(73) Assignees: INSTITUT NATIONAL DE LA SANTE ET DE LA RECHERCHE MEDICALE (INSERM), Paris (FR); Centre National de la recherche scientifique, Paris (FR); Université Pierre et Marie Curie, Paris (FR); Université Paris Diderot, Paris (FR); ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 574 days.

(21) Appl. No.: 15/761,486
(22) PCT Filed: Sep. 23, 2016
(86) PCT No.: PCT/EP2016/072769
§ 371 (c)(1),
(2) Date: Mar. 20, 2018
(87) PCT Pub. No.: WO2017/051014
PCT Pub. Date: Mar. 30, 2017

(65) Prior Publication Data
US 2018/0261127 A1 Sep. 13, 2018

(30) Foreign Application Priority Data

Sep. 25, 2015 (EP) ..................................... 15306501

(51) Int. Cl.
*G09B 23/28* (2006.01)
*A61B 8/08* (2006.01)
(Continued)

(52) U.S. Cl.
CPC .............. *G09B 23/286* (2013.01); *A61B 8/00* (2013.01); *A61B 8/06* (2013.01); *A61B 8/0816* (2013.01);
(Continued)

(58) Field of Classification Search
CPC ....... A61B 5/16; A61B 5/4064; A61B 8/0808; A61B 5/04009; A61B 8/00; A61B 8/06;
(Continued)

(56) References Cited

U.S. PATENT DOCUMENTS 6,018,675 A * 1/2000 Apkarian ............. A61B 5/4824
600/407
2006/0089551 A1* 4/2006 England ................. A61B 5/055
128/923
(Continued)

FOREIGN PATENT DOCUMENTS

| EP | 2101191 A2 | 9/2009 |
| WO | 2013/152035 A1 | 10/2013 |
| WO | 2014/127091 A1 | 8/2014 |

OTHER PUBLICATIONS

Sejdic Ervin et al: "A compressive sampling-approach for brain-machine interfaces based on transcranial Doppler sonography: A case study of resting-state maximal cerebral blood velocity signals", 2013 IEEE Global Conference on Signal and Information Processing, IEEE, Dec. 3, 2013, pp. 13-16.
(Continued)

*Primary Examiner* — Jack Yip
(74) *Attorney, Agent, or Firm* — WCF IP

(57) ABSTRACT

The invention relates to a method for obtaining a numerical model, the numerical model associating at least one objective measurement to a subjective sensation, the method comprising the steps of: a) imaging the at least one area of
(Continued)

the brain by using unfocused waves produced by a transcranial ultrasound probe (20), to obtain at least one acquired image of the activity of the area, b) evaluating a physical quantity representative of the activity of the at least one area based on the acquired images, to obtain at least one objective measurement, c) obtaining from the subject at least one numerical value representative of a subjective sensation, and d) determining the numerical model by using the obtained objective measurement and the obtained numerical value.

20 Claims, 1 Drawing Sheet

(51) Int. Cl.
| | | |
|---|---|---|
| *A61B 8/00* | (2006.01) | |
| *G16H 50/50* | (2018.01) | |
| *A61B 8/06* | (2006.01) | |
| *G06T 7/00* | (2017.01) | |

(52) U.S. Cl.
CPC .............. *A61B 8/42* (2013.01); *A61B 8/4209* (2013.01); *A61B 8/483* (2013.01); *G06T 7/0012* (2013.01); *G16H 50/50* (2018.01); *G06T 2207/10136* (2013.01); *G06T 2207/30016* (2013.01)

(58) Field of Classification Search
CPC ....... A61B 8/0816; A61B 8/42; A61B 8/4209; A61B 8/483; A61N 1/36025; G09B 23/286; G06T 7/0012; G06T 2207/10136; G06T 2207/30016; G16H 50/50
See application file for complete search history.

(56) References Cited

U.S. PATENT DOCUMENTS

| | | | | |
|---|---|---|---|---|
| 2006/0173338 | A1* | 8/2006 | Ma | A61B 8/00 600/456 |
| 2008/0249430 | A1* | 10/2008 | John | A61B 5/369 600/544 |
| 2009/0312817 | A1* | 12/2009 | Hogle | A61B 5/682 607/54 |
| 2012/0289869 | A1* | 11/2012 | Tyler | A61B 5/04008 601/2 |
| 2012/0296569 | A1* | 11/2012 | Shahaf | A61B 5/4064 702/19 |
| 2014/0335489 | A1* | 11/2014 | DeCharms | A61B 5/0042 434/236 |
| 2015/0313496 | A1* | 11/2015 | Connor | A61B 5/369 600/301 |
| 2015/0351655 | A1* | 12/2015 | Coleman | G16H 50/20 600/301 |
| 2016/0054409 | A1* | 2/2016 | Wager | A61B 5/055 600/411 |
| 2018/0296183 | A1* | 10/2018 | Urban | G01S 15/8995 |

OTHER PUBLICATIONS

Montaldo G et al: "Coherent plane-wave compounding for very high frame rate ultrasonography and transient elastography", IEEE Transactions on Ultrasonics, Ferroelectrics and Frequency Control IEEE, US, vol. 56, No. 3, Mar. 1, 2009, pp. 489-506.

\* cited by examiner

METHOD FOR OBTAINING A NUMERICAL MODEL ASSOCIATING AN OBJECTIVE MEASUREMENT TO A SUBJECTIVE SENSATION USING ULTRASOUND IMAGING TECHNIQUE AND ASSOCIATED DEVICE

TECHNICAL FIELD OF THE INVENTION

The present invention concerns a method for obtaining a numerical model associating at least one objective measurement to a subjective sensation. The invention also relates to an associated method for estimating a sensation of the subject. The invention also relates to a device for obtaining the numerical model.

BACKGROUND OF THE INVENTION

It is known an article by R. Christopher deCharms et al. whose title is "Control over brain activation and pain learned by using real-time functional MRI" and published in the review PNAS dated Dec. 20, 2005.

According to this article, if an individual can learn to directly control activation of localized regions within the brain, this approach might provide control over the neurophysiological mechanisms that mediate behavior and cognition and could potentially provide a different route for treating disease. Control over the endogenous pain modulatory system is a particularly important target because it could enable a unique mechanism for clinical control over pain. In this article, it is found that by using real-time functional magnetic resonance imaging (rtfMRI) to guide training, subjects were able to learn to control activation in the rostral anterior cingulate cortex (rACC), a region putatively involved in pain perception and regulation. When subjects deliberately induced increases or decreases in rACC fMRI activation, there was a corresponding change in the perception of pain caused by an applied noxious thermal stimulus. Control experiments demonstrated that this effect was not observed after similar training conducted without rtfMRI information, or using rtfMRI information derived from a different brain region, or sham rtfMRI information derived previously from a different subject. Chronic pain patients were also trained to control activation in rACC and reported decreases in the ongoing level of chronic pain after training. These findings show that individuals can gain voluntary control over activation in a specific brain region given appropriate training, that voluntary control over activation in rACC leads to control over pain perception, and that these effects were powerful enough to impact severe, chronic clinical pain.

However, carrying out real-time functional magnetic resonance imaging requires the use of an imager adapted to achieve real-time functional magnetic resonance. Such imager is not accessible for a home practice, which renders such technique difficult to implement in practice. This results in the fact that many experiments requiring multiple uses of the imager are not carried out.

SUMMARY OF THE INVENTION

The invention aims at improving the access and the use of data relative to the activity of an area of the brain.

To this end, the invention concerns a method for obtaining a numerical model which associates at least one objective measurement to a subjective sensation. An objective measurement is a measurement of a physical quantity representative of the activity of at least one area of the brain of a subject. The sensation is only evaluable by the subject in term of numerical values. The method comprises the steps of:

a) imaging the at least one area of the brain by using unfocused waves produced by a transcranial ultrasound probe, to obtain at least one acquired image of the activity of the area, b) evaluating a physical quantity representative of the activity of the at least one area based on each acquired image, to obtain at least one objective measurement, c) obtaining from the subject at least one numerical value representing a subjective sensation, and d) determining the numerical model by using the obtained objective measurement and the obtained numerical value.

The use of a transcranial ultrasound probe producing unfocused waves instead of an imager adapted to achieve real-time functional magnetic resonance is more convenient for a home practice and enables determining and using the numerical model outside of the magnetic resonance imager.

According to further aspects of the invention which are advantageous but not compulsory, the method for obtaining might incorporate one or several of the following features, taken in any technically admissible combination:

the sensation is only evaluable by the subject in term of numerical values with the help of a subjective scale.

step c) is carried out with the help of a subjective scale.

each numerical values is included in a numeric scale.

the numerical model is chosen among the group consisting of a linear function, a non-linear function and a model derived from the objective measurements of the subject and numerical value representative of the subjective sensation felt by subject and from a database comprising numerical models for other subjects.

the numerical model is a model derived from both the objective and subjective measurements of the subject and from a database of other subjects.

the numerical model is a linear function with a slope equal to 1.

the evaluating step comprises defining at least one interest area based on the information provided by the image and the physical quantity representative of the activity of the area is chosen in the group consisting of the blood flow activity in the at least one interest area, the blood flow velocity in the at least one interest area and blood volume in the at least one interest area.

the evaluating step comprises defining at least one interest area based on the information provided by the image and the physical quantity representative of the activity of the area is chosen in the group consisting of the blood flow activity in the at least one interest area, the cerebral blood flow velocity in the at least one interest area and cerebral blood volume in the at least one interest area.

the objective measurement of step b) is chosen among the group consisting of a physical quantity, a correlation between an external event and a physical quantity, the correlation of physical quantities of several areas and a correlation between other measurements and a physical quantity.

the image obtained at the step a) is a three-dimensional image of the area.

the step a) of imaging comprises positioning the transcranial ultrasound probe, notably by using a vascular tree and one element chosen in the group consisting of a database, a neuronavigation tool and a helmet.

a firing rate is defined for the unfocused waves, the unfocused ultrasound firing rate of the step a) being superior to 500 Hz.

the unfocused waves are plane waves or divergent waves.

the area is the anterior cingulate cortex (ACC).

the imaging step comprises the step of:
  emitting p incident acoustic waves by the transcranial ultrasound probe (20), p being an integer superior or equal to 2, the p incident acoustic waves being obtained by a linear combination of p elementary incident waves $E_{0i}(t)$, the linear combination corresponding to the following mathematical relation:

$$E(t) = M_{coding} * E_0(t)$$

wherein:
    $M_{coding}$ is a square matrix of order p, called coding matrix,
    E(t) is a vector whose components are the p incident waves, and
    $E_0(t)$ is a vector whose components are the p elementary incident waves,
  each elementary incident waves being an unfocused wave.
    receiving by the transcranial ultrasound probe p reflected waves $R_i(t)$ corresponding to the reflection of the p incident waves by the area of the brain,
    determining the p elementary reflected waves $R_{0i}(t)$ by linearly combining the p reflected waves $R_i(t)$ by using the following mathematical relation:

$$R_0(t) = M_{decoding} * R(t)$$

wherein:
    $M_{decoding}$ is a square matrix of order p, called decoding matrix, the coding matrix $M_{coding}$ and the decoding matrix $M_{decoding}$ being such that the product of both matrices is equal to a diagonal matrix D of order p for which each diagonal component is different from zero,
    R(t) is a vector whose components are the p reflected waves, and
    $R_0(t)$ is a vector whose components are the p elementary reflected waves,
  constructing the image by using the n elementary reflected waves $R_{0i}(t)$.

The invention also relates to a method for estimating a sensation felt by a subject, the sensation being only evaluable by the subject in term of numerical values, the method comprising:
  at a first instant, the step of carrying out the method for obtaining a numerical model, the numerical model associating at least one objective measurement to a subjective sensation, the method being as previously described,
  at a second instant posterior to the first instant, the steps of:
    imaging the at least one area of the brain by using unfocused waves produced by a transcranial ultrasound probe, to obtain at least one second acquired image of the activity of the area,
    evaluating a physical quantity representative of the activity of the at least one area based on each second acquired image, to obtain at least one second objective measurement, and
    estimating the sensation felt by the subject by using the numerical model applied on the second objective measurement, the numerical model being the model obtained at the first instant.

The specification also describes a device for obtaining a numerical model, the numerical model associating at least one objective measurement to a subjective sensation, an objective measurement being a measurement of a physical quantity representative of the activity of at least one area of the brain of a subject, the sensation being only evaluable by the subject in term of numerical values, the device comprising an imaging unit adapted to image the at least one area by using unfocused waves produced by a transcranial ultrasound probe, the transcranial ultrasound probe being adapted to produce unfocused waves to obtain at least one acquired image of the area. The device also comprises a controller adapted to evaluate a physical quantity representative of the activity of the at least one area based on each acquired image, to obtain at least one objective measurement, and a controller adapted to determine the numerical model by using the obtained objective measurement and a numerical value, the numerical value being obtained by obtaining from the subject at least one numerical value representative of a subjective sensation.

According to further aspects of the invention which are advantageous but not compulsory, the device might incorporate one or several of the following features, taken in any technically admissible combination:
  the controller comprises a memory storing a database built from other subjects and is adapted to access the database to determine the numerical model.
  the controller is further adapted to provide a signal representative of the evolution of the sensation based on the each acquired image of the area.
  the device further comprises a feedback unit, the feedback unit (18) fulfilling at least one of the following properties:
  i) the feedback unit is adapted to convert a signal in a perceptible signal for a user,
  ii) the feedback unit is adapted to provide a perceptible signal to the user chosen in the group consisting of a visual signal, an aural signal, an haptic signal, a vibration signal and a digital signal, and
  iii) the feedback unit is chosen in the group consisting of a tv set, a hifi system, a computer, a smartphone, an electronic device, a computer program, a domotic system and a video game.

The specification also describes a method for treating a state characterized by a subjective sensation which an area of a brain of a subject is devoted to, the method for treating comprising using a numerical model determined by the method for obtaining as previously described.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

Figure 1:
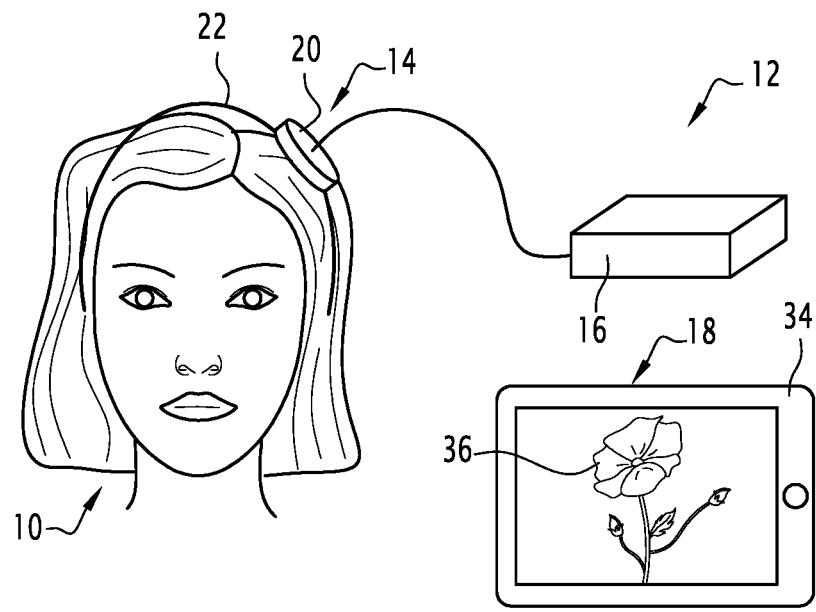
FIG. 1 shows schematically a subject and a device for obtaining a numerical model.

A subject 10 and a device 12 are represented on FIG. 1.

The subject 10 is a human being.

Alternatively, the subject 10 is an animal.

The device 12 is a device for monitoring the activity of at least an area of the brain of the subject 10.

According to the example of FIG. 1, the area is the anterior cingulate cortex (also named after the acronym ACC).

The anterior cingulate cortex is the frontal part of the cingulate cortex that resembles a "collar" surrounding the frontal part of the corpus callosum. It consists of Brodmann areas 24, 32, and 33. It appears to play a role in a wide variety of autonomic functions, such as regulating blood pressure and heart rate. It is also involved in rational cognitive functions, such as reward anticipation, decision-making, empathy, impulse control, and emotion.

In a specific embodiment, the area is the rostral anterior cingulate cortex.

Alternatively, the area is the area of the brain devoted to the chronic pain.

According to another embodiment, the area is the area of the brain devoted to the addiction.

Alternatively, the area is the area auditory cortex-tinnitus.

According to another embodiment, the area is the area motor cortex—stroke.

Alternatively, the area is the area ventrolateral prefrontal cortex and insula—depression.

According to another embodiment, the area is the supplementary motor area and the parahippocampal cortex which may be responsible for motor reaction times and memory encoding.

Alternatively, the area is the visual cortex which may be responsible for hemispatial neglect, dyslexia, or mood disorders.

According to another embodiment, the area is amygdala which is responsible for major depressive disorder and emotion control.

The activity of an area is generally linked to the blood flow in the area.

As an example, the activity is evaluated by considering the blood volume in the area.

As another example, the activity is evaluated by considering the blood flow velocity in the area.

As another example, the activity is evaluated by considering the blood flow activity in the area.

When the area is related to the brain, the activity is evaluated by considering, in the area, the cerebral blood volume, the cerebral blood flow velocity and the cerebral blood flow activity.

The device 10 comprises an imaging unit 14, a controller 16 and a feedback unit 18.

The imaging unit 14 is adapted to image the area to obtain at least an image of the area.

In this example, the image obtained is a bi-dimensional image.

According to the specific example of FIG. 1, the imaging unit 14 comprises a transcranial ultrasound probe 20 and a supporting arm 22.

The transcranial ultrasound probe 20 is adapted to produce unfocused waves.

In the example, the ultrasound transducer 20 is an array of ultrasound transducers.

The number of ultrasound transducers is named n.

The number n is, for instance, comprised between 64 and 256.

To obtain a bi-dimensional image, the array of ultrasound transducers is a one-dimension bar.

The supporting arm 22 is adapted to support the transcranial ultrasound probe 20.

The transcranial ultrasound probe 20 is adapted to be moved along the supporting arm 22.

According to the specific example of FIG. 1, the transcranial ultrasound probe 20 comprises a body delimiting an aperture having a shape which is complementary to the supporting arm 22.

Figure 2:
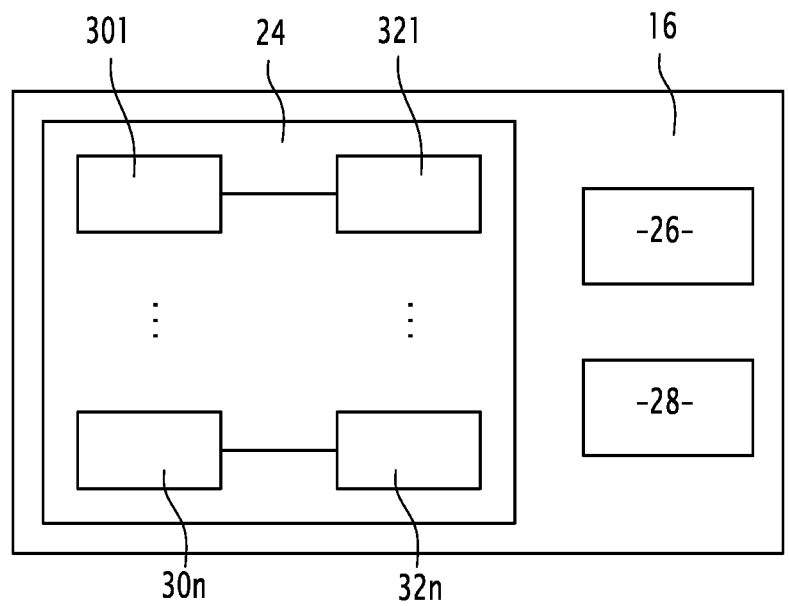
FIG. 2 shows schematically a part of the device of FIG. 1.

The controller 16 is schematically represented on FIG. 2.

The controller 16 is adapted to evaluate the activity of the area based on the at least one image obtained by the imaging unit 14.

The controller 16 is further adapted to determine a numerical model by using the obtained objective measurement and the numerical value, the numerical value being obtained from the subject.

This numerical model and the associated notions are defined when describing how the device 12 operates.

The controller 16 is further adapted to provide a signal representative of the evolution of the sensation based on the numerical model and at least one objective measurement, The controller 16 comprises an electronic circuitry 24, a processor 26 and a memory 28.

The electronic circuitry 24 is adapted to command the transcranial ultrasound probe 20.

Notably, the electronic circuitry 24 is adapted to make the array of ultrasound transducers emit ultrasound waves and receive the ultrasound waves reflected by the brain of the subject 10.

According to the specific example of FIG. 2, the electronic circuitry 24 comprises n analogue-to-digital converters 30 and n buffer memory 32.

Each analogue-to-digital converter 30 is connected to a respective ultrasound transducer of the transcranial ultrasound probe 20. In the FIG. 2, only the first analogue-to-digital converter 301 and the n-th analogue-to-digital converter 30n are represented.

Similarly, each buffer memory 32 is connected to a respective analogue-to-digital converter 30. In the FIG. 2, only the first buffer memory 321 and the n-th buffer memory 32n are represented.

The processor 26 is adapted to communicate with the buffer memories 32 and the feed-back unit 18.

The processor 26 is further adapted to process the ultrasound signals received by the transcranial ultrasound probe 20.

The memory 28 is connected to the processor 26 and is adapted to store data.

For instance, in an embodiment, the memory 28 stores a database built from other subjects, that is a set of numerical model of different subjects. In such case, the controller is adapted to use the database to determine the numerical model.

The feedback unit 18 is adapted to convert a signal in a perceptible signal for a user.

In this circumstance, the signal converted is the signal provided by the controller 16.

By perceptible, it is meant a signal that can be perceived by a human being.

For instance, the feedback unit 18 is adapted to provide a perceptible signal chosen in the group consisting of a visual signal, an aural signal, an haptic signal and a vibration signal.

In general, the user is the subject 10.

In a specific embodiment, the user is a human being, notably if the subject 10 is a mouse or a baby which cannot speak.

According to the specific example of FIG. 1, the feedback unit 18 is a digital tablet 34.

In the specific example, the signal is a visual signal representing a flower 36.

The flower 36 has a dimension proportional to the evaluated activity.

When the evaluated activity increases, the dimension of the flower 36 increases.

Alternatively, the feedback unit 18 is adapted to generate a visual signal with a changing color.

According to another embodiment, the feedback unit 18 is adapted to generate a sound with changing frequencies.

In another embodiment, the feedback unit 18 is adapted to modify a music, video or animated images sequence or light bulb colors to produce a different ambiance.

Alternatively, the feedback unit 18 is adapted to generate at least one element among the element belonging to the group consisting of an image or sequence of animated images, a sound or real time modification of a sound, a music or real time modification of music, a video or real time modification of a video, an artificially generated music, an artificially generated video or animated sequence, an artificially generated virtual reality world or object, an artificially generated augmented reality world or object, and an haptic or vibration feedback.

More generally, the feedback unit 18 is any element adapted to provide a tailored feedback to help the subject maintain or alter a sensation level.

In another embodiment, the feedback unit 18 is chosen in the group consisting of a computer, a smartphone, a tablet, a wearable device program, a video game software, a video game device, a tv, a tv channel, a HiFi system, a playlist, a website, a communication software or device, a robotic toy, a domotic system, an alarm system, a lighting system, a website or program to track and/or share achievements, an haptic feedback device, a virtual reality device, an augmented reality device, an electrical stimulation device, an ultrasonic stimulation device, a robotic massage chair, a motorized bed, a robotic sculpture, a motorized wheelchair, an exoskeleton, a cooling device and a heating device.

More generally, the feedback unit 18 is any element adapted to provide a tailored experience to help the subject 10 maintain or alter a sensation level.

According to another embodiment, the feedback unit 18 is used with a handheld device, tablet device, television set or virtual reality helmet.

In summary, the feedback unit 18 fulfills at least one of the following properties:
  i) the feedback unit 18 is adapted to convert a signal in a perceptible signal for a user,
  ii) the feedback unit 18 is adapted to provide a perceptible signal to the user chosen in the group consisting of a visual signal, an aural signal, an haptic signal, a vibration signal and a digital signal, and
  iii) the feedback unit 18 is chosen in the group consisting of a tv set, a hifi system, a computer, a smartphone, an electronic device, a computer program, a domotic system and a video game.

Operation of the device 12 is now described in reference to an example of carrying out of a method for obtaining a numerical model.

The numerical model associates at least one objective measurement to a subjective sensation.

Before describing in more details the method for obtaining, the notions of "objective measurement", "subjective sensation" and "numerical model" are first defined.

An objective measurement is a measurement of a physical quantity representative of the activity of at least one area of the brain of the subject 14.

As explained previously, the physical quantity is, for instance, representative of the activity of the area and is chosen in the group consisting of the blood flow activity in the at least one interest area, the blood flow velocity in the at least one interest area and blood volume in the at least one interest area.

In such circumstances, in an embodiment, the objective measurement is one of the physical quantities. This means that the objective measurement is representing the functional activation of one or several areas.

In another embodiment, the objective measurement is a correlation between an external event and a physical quantity. This means that the objective measurement is representing the functional response of one or several areas. An external event is, for instance, the instant of generation of a stimulus.

In another embodiment, the objective measurement is a correlation of physical quantities of several areas. This means that the objective measurement is representing the functional coactivation/connectivity of several areas.

In another embodiment, the objective measurement is a correlation between other measurements and a physical quantity. For instance, it may be considered to correlate electroencephalographic measurements with blood flow activity.

In other words, it is advantageous that the objective measurement be chosen among the group consisting of a physical quantity, a correlation between an external event and a physical quantity, the correlation of physical quantities of several areas and a correlation between other measurements and a physical quantity.

A sensation is a set of perception associated with stimulation of a sense organ.

Pain is a typical example of sensation.

Heat and luminosity are other examples of sensation.

In this context, the sensation is qualified as subjective sensation because the sensation is relative to a subject.

The sensation is only evaluable by the subject 10 in term of numerical values.

This means that the subject 10 is not able to quantify the sensation in an objective manner.

The subject 10 is only able to compare the sensation with another sensation.

This ability is independent from the ability of the experimenter to quantify the stimulation.

For instance, pain cannot be measured by an experimenter while the temperature (for heat) can be measured by a thermometer and the luminosity can also be measured.

The set of possible numerical values form a subjective scale.

The numerical model is a function.

For instance, the model is a linear function.

In an alternative embodiment, the model is a linear function with a slope equal to 1.

In another embodiment, the model is a model derived from the objective and subjective measurements of the subject and from a database of other subjects.

Alternatively, the model is a non-linear function.

An example of method for obtaining is now detailed.

The method for obtaining the numerical model comprises an imaging step, an evaluating step, an obtaining step and a determining step.

At the imaging step, the anterior cingulate cortex is imaged by using unfocused waves produced by the transcranial ultrasound probe 20 to obtain at least one two-dimensional image of the anterior cingulate cortex.

An unfocused ultrasound wave is a wave for which an aperture is defined.

The aperture has a specific size labeled D.

An ultrasound wave is considered as unfocused if the minimal width $W_{min}$ of the ultrasound beam associated to the ultrasound wave at a depth F is larger than the ratio of the product of the wavelength λ of the ultrasound wave by the depth F with the specific size D of the aperture. Such condition may be mathematically expressed as:

$$W_{min} > \frac{\lambda * F}{D}$$

This means that the unfocused waves are plane waves or divergent waves.

According to a specific example, the image area obtained at the imaging step is superior or equal to 1.0 cm².

Preferably, the firing rate of the imaging step is superior to 500 Hz.

The firing rate corresponds to the number of unfocussed emissions that are emitted in a given period of time.

In the specific example described, the imaging step comprises a positioning step, an emitting step, a receiving step, a determining step and a constructing step.

At the positioning step, the transcranial ultrasound probe 20 is positioned for enabling to image the anterior cingulate cortex.

Such positioning step is, for instance, carried out by using a vascular tree.

As a specific example, the positioning step comprises four substeps.

The first substep is a substep of vascular imaging during which the brain of the subject 10 is imaged by ultrasound imaging, to obtain a vascular image to be studied.

The second substep is a substep of localization during which the vascular image to be studied is compared with a cerebral vascular atlas by pattern recognition.

The atlas "Paxinos" are examples of cerebral vascular atlas.

The third substep is a substep of identification during which a cerebral functional atlas corresponding to the cerebral vascular atlas is used to localize the anterior cingulate cortex and to determine the position where the transcranial ultrasound probe 20 should be to obtain an image of the anterior cingulate cortex.

The fourth substep is a substep of moving the transcranial ultrasound probe 20 at the determined position.

During the emitting step, a series of incident acoustic waves are emitted by the transcranial ultrasound probe 20.

The number of incident acoustic waves emitted during the emitting step is labeled the integer p.

The integer p is an integer superior or equal to 2.

According to a specific embodiment, the integer p is even.

As an example, the integer p is comprised between 2 and 100.

Advantageously, the integer p is comprised between 4 and 20.

The incident acoustic waves are pulses whose duration is inferior or equal to 1 microsecond (μs).

According to a specific example, the duration of each pulse is comprised between one to ten cycles of the ultrasound wave at the central frequency.

The period of time between two consecutive emissions of ultrasound waves is comprised between 50 μs and 200 μs.

The incident acoustic waves are obtained by a linear combination of p elementary incident waves $E_{0i}(t)$.

Each elementary incident wave is an unfocused wave.

More precisely, the linear combination corresponds to the following mathematical relation:

$$E(t) = M_{coding} * E_0(t)$$

wherein:

$M_{coding}$ is a coding matrix,

E(t) is a vector whose components are the p incident waves, and $E_0(t)$ is a vector whose components are the p elementary incident waves.

The coding matrix $M_{coding}$ is a square matrix of order p.

According to an embodiment, the matrix $M_{coding}$ is proportional to a Hadamard matrix.

Mathematically, this means that $M_{coding} = k \cdot H_p$ wherein:

k is non-zero constant, and $H_p$ is an Hadamard matrix of order p.

In mathematics, a Hadamard matrix, named after the French mathematician Jacques Hadamard, is a square matrix whose entries are either +1 or −1 and whose rows are mutually orthogonal. In geometric terms, this means that every two different rows in a Hadamard matrix represent two perpendicular vectors, while in combinatorial terms, it means that every two different rows have matching entries in exactly half of their columns and mismatched entries in the remaining columns. It is a consequence of this definition that the corresponding properties hold for columns as well as rows. The n-dimensional parallelotope spanned by the rows of an p×p Hadamard matrix has the maximum possible p-dimensional volume among parallelotopes spanned by vectors whose entries are bounded in absolute value by 1. Equivalently, a Hadamard matrix has maximal determinant among matrices with entries of absolute value less than or equal to 1 and so, is an extremal solution of Hadamard's maximal determinant problem.

For instance, $$H_2 = \begin{bmatrix} 1 & 1 \\ 1 & -1 \end{bmatrix} \text{ and } H_4 = \begin{bmatrix} 1 & 1 & 1 & 1 \\ 1 & -1 & 1 & -1 \\ 1 & 1 & -1 & -1 \\ 1 & -1 & -1 & 1 \end{bmatrix}$$

are two examples of Hadamard matrix for a value of the integer p respectively equal to 2 and to 4.

In the specific embodiment described, the matrix $M_{coding}$ is a Hadamard matrix.

According to another embodiment, the p incident acoustic waves are calculated in advance and stored in the memory 28.

The incident acoustic waves sent to the anterior cingulate cortex propagates in the anterior cingulate cortex before being reflected by the anterior cingulate cortex.

p reflected waves $R_i(t)$ are obtained.

At the receiving step, the p reflected waves $R_i(t)$ are received by the transcranial ultrasound probe 20.

At the determining step, p elementary reflected waves $R_{0i}(t)$ are determined.

For example, the p elementary reflected waves $R_{0i}(t)$ are obtained by a linear combination of n reflected waves $R_i(t)$.

More precisely, the combination corresponds to the following mathematical relation:

$$R_0(t) = M_{decoding} * R(t)$$

wherein:

$M_{decoding}$ is a decoding matrix,

R(t) is a vector whose components are the p reflected waves, and $R_0(t)$ is a vector whose components are the p elementary reflected waves.

The decoding matrix $M_{decoding}$ is a square matrix of order p.

The coding matrix $M_{coding}$ and the decoding matrix $M_{decoding}$ are such that the product of both matrices is equal to a diagonal matrix D, which corresponds to:

$$M_{coding} * M_{decoding} = D$$

In the specific embodiment described, the decoding matrix $M_{decoding}$ is the transpose matrix of the coding matrix $M_{coding}$.

According to a specific embodiment, D is a diagonal matrix of order p whose each diagonal component is different from zero.

According to another embodiment, each diagonal component of the diagonal matrix D is superior or equal to 1.

In the specific embodiment of FIG. 1, the diagonal matrix D is equal to the product of the integer p by the identity matrix. In other words, each diagonal component of the diagonal matrix D is equal to the integer p.

At the constructing step, an image of the anterior cingulate cortex is obtained by using the p elementary reflected waves $R_{0i}(t)$.

Such constructing step is, for instance, carried out as described in the document EP 2 101 191 or in the article by Montaldo et al. whose title is "*Coherant plane-wave compounding for very high frame rate ultrasonography and transient elastography*" in IEEE Trans Ultrason Ferroelectr Freq Control 2009 March, 56(3), 489-506.

At the evaluating step, the activity of the anterior cingulate cortex is evaluated based on the image.

In other words, at the evaluating step, a physical quantity representative of the activity of the anterior cingulate cortex is evaluated based on the acquired images. This enables to obtain at least one objective measurement.

The evaluating step is carried out by the controller 16.

For instance, the evaluating step comprises defining an interest area based on the information provided by the image and evaluating the blood flow in the defined interest area.

In such embodiment, the objective measurements are, for instance, the average cerebral blood volume or cerebral blood flow of predetermined brain structures obtained by transcranial Doppler using unfocused waves.

At the obtaining step, at least one numerical value representative of a subjective sensation is obtained from the subject 10.

The obtaining step may be carried out directly or indirectly.

For instance, the obtaining step may be achieved thanks to a self-report scale such as a visual analog scale. Such self-report scale or visual analog scale are subjective scales.

At the determining step, the numerical model is determined by using the obtained objective measurement and the obtained numerical value.

For instance, the numerical model is a function with parameters and the determining step is carried out by numerically determining the parameters.

A least damped square optimization technique may be used to obtain the searched parameters.

Alternatively, a learning method may be used. For instance, a supervised technique may be advantageously considered.

The method for obtaining a numerical model applied to the anterior cingulate cortex enables to obtain a numerical model which enables to relate the blood flow with the pain of the subject 10.

Such method should not be confused with a neurostimulation method as disclosed in document WO 2013/152035 A1. Indeed, in such document, the ultrasound waves are not use to image the cortex but rather to modify the neuronal state without any intervention of the patient. In some case, the patient can even be sleeping. In other words, in such document, there is an external modification of the neuronal state by a biophysical interaction between the ultrasound waves and the neuronal tissue.

By contrast, in the present invention, the numerical model is constructed on the basis of observation of the awaken patient. The only modification of the neuronal state is made by the patient by a conscious working. Similar remarks apply to the document WO 2014/127091 A2 when compared with the present invention.

In addition, the use of a transcranial ultrasound probe 20 producing unfocused is convenient for a home practice since the transcranial ultrasound probe 20 is light and occupies a small volume.

Such method for obtaining a numerical model applied to the anterior cingulate cortex is therefore easier to implement in practice than previous methods.

Furthermore, with comparison to the document US 2014/335489 A1, such method is provides a better sensitivity since classical Doppler only gives access to flux variations of huge blood vessels. In other words, this means that classical Doppler cannot be used to image the neuronal activity. Such difference in the quality of the image is notably known from article by Emilie Mace et al. whose title is "*Functional Ultrasound Imaging of the Brain: Theory and Basic Principles*" which was published in the review IEEE Transactions On Ultrasonics, Ferroelectrics, and Frequency Control, Volume 60, Number 3 and dated March 2013.

This renders possible that such method can be used to determine the pain felt by the subject 10 without any input from the subject 10.

For instance, it can be considered a method for estimating a sensation felt by the subject 10 at a time ulterior to the determination of the numerical model.

In such method, for instance, at a first instant, the method for obtaining a numerical model is carried out.

Then, at a second instant posterior to the first instant, the method for estimating comprises a step of imaging, a step of evaluating and a step of estimating.

At the step of imaging, the at least one area of the brain considered in the method for obtaining is imaged. This imaging step is carried out by using unfocused waves produced by a transcranial ultrasound probe 20, to obtain at least one second acquired image of the activity of the area.

At the step of evaluating, a physical quantity representative of the activity of the at least one area based on each second acquired image, to obtain at least one second objective measurement.

Preferably, the second objective measurement corresponds to the objective measurement for which the numerical model has been determined at the first instant. This avoids using an additional operation.

At the step of estimating, the sensation felt by the subject is estimated by using the numerical model applied on the second objective measurement, the numerical model being the model obtained at the first instant. At the end of the estimating step, a numerical value is obtained.

In other words, the obtained model is used to quantitatively estimate the level of a given sensation from a new set of objective measurements without the need for the subject to subjectively and consciously assess his sensation.

According to a preferred embodiment, the estimating method also comprises a step of generating a signal representative of the sensation.

The generating step is carried out by the feedback unit 18.

In the present case, the signal is the height of the flower 36.

This method also opens the way to achieving at home a method for reducing the pain by controlling the activity of the anterior cingulate cortex. The subject 10 only has to increase the size of the flower 36 for activating the anterior cingulate cortex which helps him focusing on reducing his pain.

Another way of exploiting such model is a method for reducing pain of a subject comprising using the numerical model.

For instance, two numerical models may be used to quantify in an objective way the reduction obtained.

In a more general way, it can be considered a method for treating a state characterized by a subjective sensation which an area of a brain of a subject is devoted to, the method for treating comprising using the numerical model.

Indeed, such method for determining a numerical model can be applied to any area of the brain.

In this context, the state may be the presence of a disease or a behavior state.

Insomnia, attention-deficit disorder (ADD) or attention-deficit hyperactivity disorder (ADHD) are concrete example of a state related to the presence of a disease.

Addiction is a behavior state.

As a specific example, the method may treat depression by a work on the sadness felt by the subject 10 as subjective sensation.

Similarly, the method may treat addiction to alcohol by a work on the miss feeling felt by the subject 10 as subjective sensation.

According to another embodiment, the imaging unit 14 is adapted to image the area to obtain at least one tri-dimensional image of the area and the array of ultrasound transducers is a bi-dimensional array.

Alternatively, the image obtained at the step of imaging is a three-dimensional image of the area.

Three-dimensional images enable to obtain a more relevant ultrasound signal resulting in a better evaluation of the activity of the considered area.

The embodiments and alternative embodiments considered here-above can be combined to generate further embodiments of the invention.

The invention claimed is:

1. A method for estimating a sensation felt by a subject, the sensation being only evaluable by the subject in terms of numerical values, the method comprising:
   at a first instant:
   a) imaging the at least one area of the brain by using unfocused acoustic waves produced by a transcranial ultrasound probe, to obtain at least one acquired image of the activity of the area,
   b) evaluating a physical quantity representative of the activity of the at least one area based on each acquired image, to obtain at least one objective measurement, an objective measurement being a measurement of a physical quantity representative of the activity of at least one area of the brain of the subject,
   c) obtaining from the subject at least one numerical value representative of the sensation felt by the subject, and
   d) determining a numerical model specific to the subject by using the obtained objective measurement and the obtained numerical value, the numerical model associating to at least one objective measurement the numerical value of the sensation felt by the subject,
   wherein the numerical model is selected from the group consisting of:
   a linear function and
   a non-linear function;
   at a second instant posterior to the first instant, the steps of:
   e) imaging the at least one area of the brain of the subject by using unfocused acoustic waves produced by a transcranial ultrasound probe, to obtain at least one second acquired image of the activity of the area of the brain of the subject,
   f) evaluating a physical quantity representative of the activity of the at least one area based on each second acquired image, to obtain at least one second objective measurement, specific to the subject obtained at the first instant,
   g) estimating the sensation felt by the subject by using the numerical model specific to the subject obtained at the first instant, the linear function or the non-linear function of the numerical model specific to the subject obtained at the first instant taking as an input the second objective measurement,
   h) providing a feedback unit with a signal representative of the estimated sensation felt by the subject, the feedback unit being selected from the group consisting of a tv set, a hifi system, a computer, a smartphone, an electronic device, a computer program, a domotic system, and a videogame,
   i) converting the signal representative of the estimated sensation felt by the subject into a corresponding signal perceptible by the subject, said step of converting being carried out by the feedback unit, said corresponding signal perceptible by the subject being tailored feedback to help the subject maintain or alter a sensation level and the signal perceptible to the subject being chosen in the group consisting of a visual signal, an aural signal, an haptic signal, a vibration signal and a digital signal unit, and
   j) providing the subject with said corresponding signal perceptible by the subject, the step of providing said corresponding signal perceptible by the subject being carried out by the feedback unit so that the subject can maintain or alter the sensation.

2. The method according to claim 1, wherein the evaluating step comprises defining at least one interest area based on the information provided by the image and the physical quantity representative of the activity of the area is chosen in the group consisting of the blood flow activity in the at least one interest area, the blood flow velocity in the at least one interest area and blood volume in the at least one interest area.

3. The method according to claim 2, wherein the objective measurement of step b) is chosen among the group consisting of a physical quantity, a correlation between an external event and a physical quantity, the correlation of physical quantities of several areas and a correlation between other measurements and a physical quantity.

4. The method according to claim 1, wherein the image obtained at the step a) is a three-dimensional image of the area.

5. The method according to claim 1, wherein the step a) of imaging comprises positioning the transcranial ultrasound probe, notably by using a vascular tree and one element chosen in the group consisting of a database, a neuronavigation tool and a helmet.

6. The method according to claim 1, wherein a firing rate is defined for the unfocused waves, the unfocused ultrasound firing rate of the step a) being superior to 500 Hz.

7. The method according to claim 1, wherein the unfocused waves are plane waves or divergent waves.

8. The method according to claim 1, wherein the area is the anterior cingulate cortex (ACC).

9. A method for treating a state characterized by a subjective sensation which an area of a brain of a subject is devoted to the method for treating comprising using a numerical model determined by the method for obtaining according to claim 1.

10. The method according to claim 1, wherein the imaging unit is transportable by the subject.

11. The method according to claim 1, wherein the feedback unit is transportable by the subject.

12. The method according to claim 1, wherein the feedback unit is further provided with a signal representative of the evolution of the sensation based on the each acquired image of the area, the signal perceptible by the subject being an interactive signal so that the signal perceptible to the subject rests the same when the subject maintain the sensation level and varies when the subject alter the sensation level, to help the subject maintain or alter a sensation level.

13. A method for estimating a sensation felt by a subject, the sensation being only evaluable by the subject in terms of numerical values, the method comprising:
   at a first instant:
      a) imaging the at least one area of the brain by using unfocused waves produced by a transcranial ultrasound probe, to obtain at least one acquired image of the activity of the area,
      b) evaluating a physical quantity representative of the activity of the at least one area based on each acquired image, to obtain at least one objective measurement, an objective measurement being a measurement of a physical quantity representative of the activity of at least one area of the brain of the subject,
      c) obtaining from the subject at least one numerical value representative of the sensation felt by the subject, and
      d) determining a numerical model by using the obtained objective measurement and the obtained numerical value, the numerical model associating to at least one objective measurement the numerical value of the sensation felt by the subject,
   at a second instant posterior to the first instant, the steps of:
      e) imaging the at least one area of the brain by using unfocused waves produced by a transcranial ultrasound probe, to obtain at least one second acquired image of the activity of the area,
      f) evaluating a physical quantity representative of the activity of the at least one area based on each second acquired image, to obtain at least one second objective measurement,
      g) estimating the sensation felt by the subject by using the numerical model applied on the second objective measurement, the numerical model being the model obtained at the first instant, and
      h) providing with a feedback unit a signal representative of the estimated sensation perceptible to the subject, wherein the signal representative of the estimated sensation perceptible to the subject is tailored feedback to help the subject maintain or alter a sensation level, wherein the feedback unit is selected from the group consisting of a tv set, a hifi system, a computer, a smartphone, an electronic device, a computer program, a domotic system, and a videogame,
   wherein the numerical model is chosen among the group consisting of:
      a linear function, or
      a non-linear function, and
   wherein steps a) and e) comprise the step of:
      emitting p incident acoustic waves by the transcranial ultrasound probe, p being an integer superior or equal to 2, the p incident acoustic waves being obtained by a linear combination of p elementary incident waves $E_{0i}$, (t), the linear combination corresponding to the following mathematical relation:

$$E(t) = M_{coding} * E_0(t)$$

wherein:
      $M_{coding}$ is a square matrix of order p, called coding matrix,
      E(t) is a vector whose components are the p incident waves, and
      $E_0(t)$ is a vector whose components are the p elementary incident waves,
   each elementary incident waves being an unfocused wave,
      receiving by the transcranial ultrasound probe p reflected waves $R_i(t)$ corresponding to the reflection of the p incident waves by the area of the brain,
      determining the p elementary reflected waves $R_{0i}(t)$ by linearly combining the p reflected waves $R_i(t)$ by using the following mathematical relation:

$$R_0(t) = M_{decoding} * R(t)$$

wherein:
      $M_{decoding}$ is a square matrix of order p, called decoding matrix, the coding matrix $M_{coding}$ and the decoding matrix $M_{decoding}$ being such that the product of both matrices is equal to a diagonal matrix D of order p for which each diagonal component is different from zero,
      R(t) is a vector whose components are the p reflected waves, and
      $R_0(t)$ is a vector whose components are the p elementary reflected waves,
      constructing the image by using the n elementary reflected waves $R_{0i}(t)$.

14. A device for obtaining a numerical model, the numerical model associating at least one objective measurement to a subjective sensation, an objective measurement being a measurement of a physical quantity representative of the activity of at least one area of the brain of a subject, the sensation being only evaluable by the subject in term of numerical values, the device comprising:
   an imaging unit adapted to image the at least one area by using unfocused acoustic waves produced by a transcranial ultrasound probe, the transcranial ultrasound probe being adapted to produce unfocused acoustic waves to obtain at least one acquired image of the area at a first instant and at a second instant, a controller adapted to:
   evaluate a physical quantity representative of the activity of the at least one area based on each acquired image, to obtain at least one objective measurement, and
   determine the numerical model specific to the subject by using the obtained objective measurement and a numerical value, the numerical value being obtained by obtaining from the subject at least one numerical value representative of a subjective sensation,
wherein the imaging unit and the controller are configured to at the first instant:
   a) imaging the at least one area of the brain by using the unfocused acoustic waves produced by the transcranial ultrasound probe, to obtain at least one acquired image of the activity of the area,
   b) evaluating the physical quantity representative of the activity of the at least one area based on each acquired image, to obtain the at least one objective measurement, an objective measurement being a measurement of a physical quantity representative of the activity of at least one area of the brain of the subject,
   c) obtaining from the subject at least one numerical value representative of the sensation felt by the subject, and
   d) determining the numerical model specific to the subject by using the obtained objective measurement and the obtained numerical value, the numerical model associating to at least one objective measurement the numerical value of the sensation felt by the subject,
at the second instant posterior to the first instant, the steps of:
   e) imaging the at least one area of the brain of the subject by using the unfocused acoustic waves produced by the transcranial ultrasound probe, to obtain at least one second acquired image of the activity of the area,
   f) evaluating a physical quantity representative of the activity of the at least one area based on each second acquired image, to obtain at least one second objective measurement,
   g) estimating the sensation felt by the subject by using the numerical model specific to the subject obtained at the first instant, the linear function or the non-linear function of the numerical model specific to the subject obtained at the first instant taking as an input the second objective measurement,
   wherein the device further comprises a feedback unit, the feedback unit being selected from the group consisting of a tv set, a hifi system, a computer, a smartphone, an electronic device, a computer program, a domotic system, and a videogame,
   wherein the feedback unit is configured to be provided with a signal representative of the estimated sensation felt by the subject,
   wherein the feedback unit is configured to convert the signal representative of the estimated sensation felt by the subject into a corresponding signal perceptible by the subject,
   wherein said corresponding signal perceptible by the subject is tailored feedback to help the subject maintain or alter a sensation level, the signal perceptible to the subject being chosen in the group consisting of a visual signal, an aural signal, an haptic signal, a vibration signal and a digital signal, and wherein the feedback unit is configured to provide the subject with said corresponding signal perceptible by the subject, so that the subject can maintain or alter the sensation.

15. The device according to claim 14, wherein the controller comprises a memory storing a database built from other subjects and is adapted to access the database to determine the numerical model.

16. The device according to claim 14, wherein the controller is further adapted to provide a signal representative of the evolution of the sensation based on the each acquired image of the area.

17. The device according to claim 14, wherein the imaging unit is transportable by the subject.

18. The device according to claim 14, wherein the feedback unit is transportable by the subject.

19. The device according to claim 14, wherein the controller is further adapted to provide the feedback unit with a signal representative of the evolution of the sensation based on the each acquired image of the area, the signal perceptible by the subject being an interactive signal so that the signal perceptible to the subject rests the same when the subject maintain the sensation level and varies when the subject alter the sensation level, to help the subject maintain or alter a sensation level.

20. A method for estimating a sensation felt by a subject, the sensation being only evaluable by the subject in terms of numerical values, the method comprising:
   at a first instant:
      a) imaging the at least one area of the brain by using unfocused waves produced by a transcranial ultrasound probe, to obtain at least one acquired image of the activity of the area,
      b) evaluating a physical quantity representative of the activity of the at least one area based on each acquired image, to obtain at least one objective measurement, an objective measurement being a measurement of a physical quantity representative of the activity of at least one area of the brain of the subject,
      c) obtaining from the subject at least one numerical value representative of the sensation felt by the subject, and
      d) determining a numerical model by using the obtained objective measurement and the obtained numerical value, the numerical model associating to at least one objective measurement the numerical value of the sensation felt by the subject,
   at a second instant posterior to the first instant, the steps of:
      e) imaging the at least one area of the brain by using unfocused waves produced by a transcranial ultrasound probe, to obtain at least one second acquired image of the activity of the area,
      f) evaluating a physical quantity representative of the activity of the at least one area based on each second acquired image, to obtain at least one second objective measurement,
      g) estimating the sensation felt by the subject by using the numerical model applied on the second objective measurement, the numerical model being the model obtained at the first instant, and
      h) providing with a feedback unit a signal representative of the estimated sensation perceptible to the subject, wherein the signal representative of the estimated sensation perceptible to the subject is tailored feedback to help the subject maintain or alter a sensation level, wherein steps a) and e) comprise the step of:

emitting p incident acoustic waves by the transcranial ultrasound probe, p being an integer superior or equal to 2, the p incident acoustic waves being obtained by a linear combination of p elementary incident waves $E_{0i}(t)$, the linear combination corresponding to the following mathematical relation:

$$E(t) = M_{coding} * E_0(t)$$

wherein:

$M_{coding}$ is a square matrix of order p, called coding matrix, $E(t)$ is a vector whose components are the p incident waves, and $E_0(t)$ is a vector whose components are the p elementary incident waves, each elementary incident waves being an unfocused wave, receiving by the transcranial ultrasound probe p reflected waves $R_i(t)$ corresponding to the reflection of the p incident waves by the area of the brain, determining the p elementary reflected waves $R_{0i}(t)$ by linearly combining the p reflected waves $R_i(t)$ by using the following mathematical relation:

$$R_0(t) = M_{decoding} * R(t)$$

wherein:

$M_{decoding}$ is a square matrix of order p, called decoding matrix, the coding matrix $M_{coding}$ and the decoding matrix $M_{decoding}$ being such that the product of both matrices is equal to a diagonal matrix D of order p for which each diagonal component is different from zero, R(t) is a vector whose components are the p reflected waves, and $R_0(t)$ is a vector whose components are the p elementary reflected waves, constructing the image by using the n elementary reflected waves $R_{0i}(t)$.

* * * * *